United States Patent [19]
Polanyi et al.

[11] 4,050,450
[45] Sept. 27, 1977

[54] REFLECTION STANDARD FOR FIBER OPTIC PROBE

[75] Inventors: Michael Lajos Polanyi, Webster; David Stanley Ostrowski, Dudley, both of Mass.

[73] Assignee: American Optical Corporation, Southbridge, Mass.

[21] Appl. No.: 664,345

[22] Filed: Mar. 5, 1976

[51] Int. Cl.² ............................................. A61B 5/00
[52] U.S. Cl. ..................................... 128/2 L; 356/41
[58] Field of Search ............ 128/2 L, 2 M, 9, 214 R; 356/39–41

[56] References Cited

U.S. PATENT DOCUMENTS

| | | | |
|---|---|---|---|
| 3,068,742 | 12/1962 | Hicks, Jr. et al. | 128/214 R X |
| 3,335,715 | 8/1967 | Hugenholtz et al. | 128/2 L |
| 3,807,390 | 4/1974 | Ostrowski et al. | 128/2 L X |
| 3,814,081 | 6/1974 | Mori | 128/2 L |
| 3,822,695 | 7/1974 | Takayama | 128/2 L |

Primary Examiner—Kyle L. Howell
Attorney, Agent, or Firm—Stephen A. Schneeberger; William C. Nealon; H. R. Berkenstock, Jr.

[57] ABSTRACT

A flexible fiber optic probe or catheter insertable into the cardiovasular system for monitoring blood oxygen saturation or the like is provided with an improved standard for the calibration of the catheter and its associated electro-optic equipment. The improved calibration standard is particularly suited for catheters of very small diameter, is provided by a generally tubular reflecting member aligned with and adjacent to the distal end of the catheter. The reflecting member may be vinyl tubing or the like which may be removably of fixedly positioned about the distal end of the catheter to reflect light directed thereon from the catheter when in air or a clear sterile solution for calibration.

17 Claims, 4 Drawing Figures

REFLECTION STANDARD FOR FIBER OPTIC PROBE

BACKGROUND OF THE INVENTION

1. Field of the Invention

Fiber optic probes, and particularly fiber optic catheters with particular reference to catheters intended for insertion into the cardiovascular system.

2. Description of the Prior Art

Various fiber optic probes require calibration if their intended use includes some type of measuring function. In-vivo fiber optic catheters which are sterilized before use require calibration in conjunction with their associated electro-optical equipment so that absolute values of oxygen saturation or dye concentration and/or accurate measurements of variations thereof with time are made possible in the performance of blood oxygen saturation determinations or dye dilution measurements with these catheters.

Previously, such catheter calibration has required that the distal end of the catheter be placed in a sterile suspension medium such as milk-of-magnesia which will give a fixed ratio of reflections or wavelengths of light such as 805 mu and 660 mu or others which may be used for blood oxygen saturation or dye dilution testing. This method of calibrating in-vivo catheters, however, is potentially dangerous to patients since portions of the suspension medium clinging to the catheter may become introduced into the patients blood stream. These inclusions in not being isotonic with blood and embolic, are potentially dangerous to the patient and, least wise, may adversely affect the accuracy of oxygen saturation determinations and/or other measurements taken with the in-vivo catheter and its associated equipment.

More recently, a smoothly surfaced ball was fixedly mounted in spaced relation with the end faces of the optical fibers at the distal end of the catheter for providing fixed reflections of light directed thereon from the catheter when in air or placed in clear sterile solution for calibration prior to use, as described in U.S. Pat. No. 3,807,390 issued Apr. 30, 1974 to Ostrowski and Polanyi for FIBER OPTIC CATHETER and assigned to the assignee of the present invention. The ball was supported in position by a cage affixed to the distal end of the catheter and was carried with the catheter into the patient's blood stream. However, the manufacture of the small ball and its cage, and their installation on the distal end of the catheter is complicated by the relatively small dimensions involved. For instance, some catheters may have a diameter of as little as 1 millimeter or less. Additionally, the ball and cage structure tend to make the distal end of the catheter inflexible, which may hinder the smooth passage of the catheter through small radius bends in the blood stream.

This invention makes it possible to calibrate fiber optic probes, and particularly in-vivo catheters, without the subsequent danger of introducing extraneous matter into the blood stream. Further, the present invention provides improved means for the calibration of fiber optic probes which means is readily adaptable to probes or catheters of even very small diameter and which is of relatively low cost. Still further, the present invention provides improved means for the calibration of in-vivo fiber optic catheters which means permit the distal end of the catheter to remain relatively flexible.

SUMMARY OF THE INVENTION

The objectives of this invention are accomplished by providing the fiber optic probe in this case with an improved reflecting member or standard which may be flexible, is of relatively low cost, and is easily positioned in operative relationship with the fiber end faces at the distal end of the probe. The improved reflective member includes a passage therein for alignment with the end face or faces of the optic fibers in the probe and is positioned adjacent thereto such that light emitted from the distal end of the probe is returned thereto by its diffuse reflection on the interior surface of the reflecting member. The reflecting member is of a substance which will provide a fixed ratio of reflections of wavelengths of light emitted from the distal end of the probe when the distal end and reflecting member are immersed in air or a clear liquid. By such means, the fixed ratio of reflection may be used to calibrate the probe and its associated instrumentation. Where the probe is a catheter, this calibration permits absolute measurements of oxygen saturation, for example, or other accurate measurements to be obtained. With calibration performed in a clear air environment or a clear saline solution which is isotonic with body fluids, such hazards as contamination of patient's blood or the creation of embolisms therein by residue of some calibrating suspension mediums is avoided.

In an embodiment of the invention, the reflecting member is of flexible tubing having an inside diameter sized to accept the distal end of the probe or catheter in an end thereof in removable, cooperative, embracing relationship therewith. The reflecting member may be removed from the catheter end prior to the catheter being introduced to the blood stream.

In an alternate arrangement, the reflecting member is fixed on the end of the catheter and may be introduced to the blood stream therewith. Porting in the reflecting member aids in maintaining blood flow past the optical fiber bundle end face, and the spacing between the bundle end face and the interior surface of the reflecting member is sufficient to permit accurate analysis of the blood passing therebetween. Details of the invention will be more readily understood by reference to the following description taken in conjunction with the accompanying drawings.

DESCRIPTION OF THE PREFERRED EMBODIMENTS

A fiber optic probe in the form of a catheter 10 comprises a length of cardiac catheter tubing 12 containing a bundle 14 of efferent and afferent light-conducting fibers 16. The catheter 10 may have a diameter of as little as about one millimeter for increased utility, such as in blood vessels of limited cross-sectional area and/or where increased flexibility and maneuverability are required.

Figure 1:
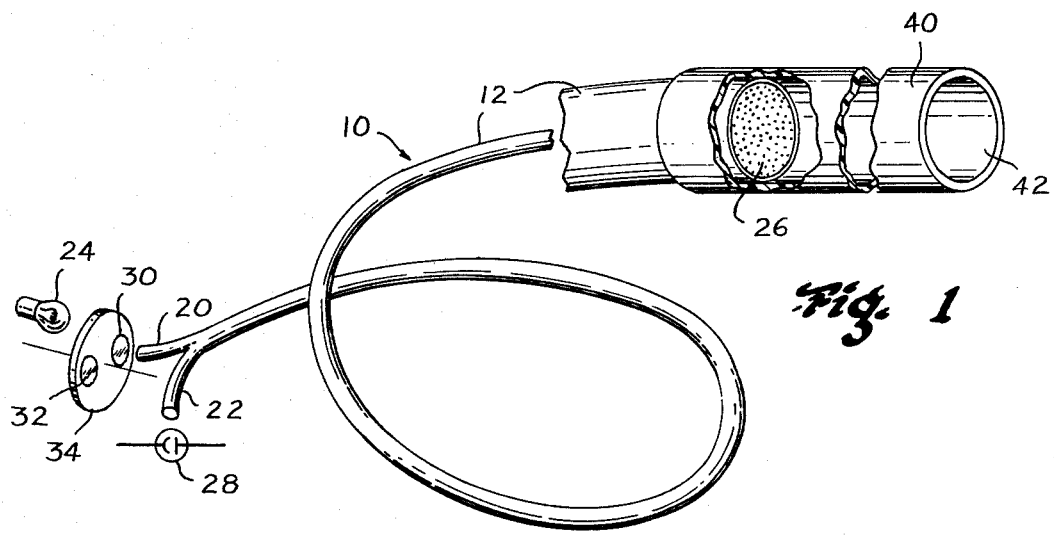
FIG. 1 is an illustration, in perspective with parts broken away and in section, of a fiber optic catheter and system of a type useful in performing in-vivo testing of blood wherein the distal end of the catheter and an improved calibration member in cooperative removable relationship therewith are shown greatly enlarged.

Conventional in catheters of this type are optical fibers 16, some of which conduct light efferently through catheter 10 toward its distal end and others of which receive and conduct light afferently toward its proximal end. These fibers in bundle 14 may be randomly intermixed adjacent the distal end of catheter 10 and respectively individually separated into branches 20 and 22 at the proximal end of catheter 10 (FIG. 1). Alternatively, they may be retained in separately bundled relationship throughout the entire length of catheter 10. Those interested in greater details of fiber optic catheter constructions and/or the construction and function of individual fibers may refer to U.S. Pat. Nos. 3,068,742 and 3,068,739.

In determining oxygen saturation of blood in-vivo with catheter 10, for example, light from lamp 24 is introduced into the optical fibers contained in one branch 20 of the catheter for conductance through the catheter and emission outwardly thereof at its face 26 directly into blood within a vessel or heart chamber of the cardiovascular system into which the catheter is inserted for this purpose. This light, upon entering the blood becomes diffusely reflected thereby back toward and partially into face 26 for reception of afferent fibers therein which convey the reflected light back through catheter 10 to and outwardly of branch 22. It is then received by a photodetector 28 from which a measurement of its intensity may be made.

To the extent that catheter 10 and its function in determing oxygen saturation of blood have been thus far described, the catheter and its associated light source and photoelectric detector 28 are conventional and explained in detail in the aforementioned U.S. Pat. Nos. 3,068,742 and 3,068,739. As is also explained in these patents, typical wavelengths of light useful in performing in-vivo oxygen saturation determinations are 805 mu and 660 mu which may be alternately or intermittently supplied to branch 20 of catheter 10 by positioning suitable light filters 30 and 32 in the path of light from lamp 24. Filters 30 and 32 may be supported in a rotating disc 34 as illustrated in FIG. 1 or in a sliding mechanism as shown and described in the aforementioned U.S. patents. Alternatively, the filters 30 and 32 may be replaced by a suitable dichroic beam splitter placed so as to receive the light returned by catheter through branch 22 and direct preselected individual wavelengths of this light along separate paths to two or more photoelectric detectors similar to detector 28 from which interpretation of the ratio of intensities of the different wavelengths of light may be accomplished for determination of blood oxygen saturation. This latter arrangement of beam splitting and individual photoelectric detection of different wavelengths of light may be found in U.S. Pat. No. 3,296,922.

In certain instances, a single fiber may be used to conduct light both efferently and afferently therethrough if the efferent light is in very short pulses, as for instance from a light emitting diode, and the associated circuitry may be rapidly switched from a transmit to a receive mode.

In order to render catheter 10 and its associated electro-optical system capable of affording absolute and/or accurate measurement of oxygen saturation or dye dilution in-vivo with each application of catheter 10 to the body, calibration of the catheter and its associated electro-optical instrumentation is required as is explained in U.S. Pat. Nos. 3,068,742; 3,068,739; and 3,296,922. This calibration, accordingly, requires that a portion of light directed through and emitted from face 26 of catheter 10 be returned therethrough with a fixed ratio of reflections, e.g. 805 mu./660 mu. As previously mentioned, this calibration has been accomplished heretofore either by placing face 26 of catheter 10 in a suspension medium of, for example, milk-of-magnesia, or more recently by using the smooth surfaced ball and placing the face 26 in air or a clear sterile saline solution as described in the aforementioned U.S. Pat. No. 3,807,390.

According to the present invention, a fixed ratio of reflections of light emitted from face 26 of catheter 10 is accomplished in air or in a clear sterile saline solution by an improved reflecting standard or member, such as tube or tubing 40 having a generally cylindrical passage 42 therein, which is suited for use with a catheter 10 having a diameter as little as 1 millimeter or less. The tube 40 is cooperatively mounted with catheter 10 during calibration such that it extends distally from the distal end of the catheter, with the passage 42 aligned or in registry with the face 26 of catheter 10. Passage 42 in tube 40 is defined by a generally cylindrical inner surface 44 from which light is diffusely reflected or scattered. Light of the preselected wavelengths is emitted from the face 26 at an angle to the axis of the catheter 10, as well as parallel thereto, as indicated by the arrows in FIGS. 2 and 4 during calibration of the catheter and associated equipment. The light emitted at an angle to the axis of catheter 10 is incident upon the inner surface 44 of calibration standard tubing 40 where upon it is scattered or diffusely reflected, as also indicated by arrows in FIGS. 2 and 4, with some of the scattered light returning to face 26.

The tube 40 may be formed of a material which provides its inner surface 44 with the characteristics needed for the scattering or diffuse reflection therefrom of some of the light from face 26. The material of tube 40 is also selected such that it will not degrade or deteriorate when exposed to gas sterilization, e.g. ethylene oxide gas, and to be non-pyrogenic. While a variety of tubing materials and colorations are satisfactory, a white-pigmented, flexible, vinyl tubing is employed in the described embodiment. It is not necessary that the inner surface 44 of tubing 40 be smooth or polished inasmuch as the diffuse reflection of light from face 26 is relied upon.

Figure 2:
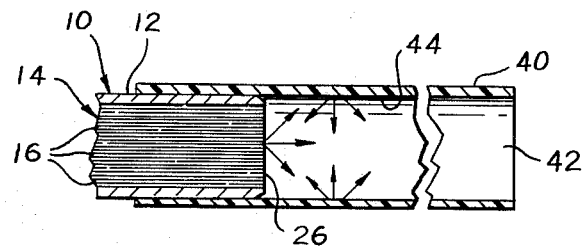
FIG. 2 is a fragmentary longitudinal cross-sectional view of the enlarged portion of the catheter and calibration member shown in FIG. 1.

The diameter of passage 42 in tube 40 is sized to receive the distal end of catheter 10 in one end thereof to establish the cooperative relationship therebetween, illustrated in FIGS. 1 and 2, which exists at least during calibration of the catheter and its electro-optical equipment. In the embodiment of the invention illustrated in FIGS. 1 and 2, the tube 40 is at least slightly elastic and sized to removably embrace the catheter tubing 12 such that it is retained cooperatively positioned during calibration of the catheter and is removable therefrom thereafter. It will be appreciated that a tube 40 having a larger diameter passage 42 might also be used, with releasable connecting means serving to removably mount the tube to the catheter 10. The tube 40 is of sufficient length and rigidity that the directions and intensities of light reflected to face 26 are substantially fixed and constant, even though a different piece of tubing 40 of the same color might be used in a subsequent calibration. Typically, substantially all of the light of the utilized wavelenghts which may be returned to face 26 by the inner surface 44 is done so by that length of tubing 40 which extends beyond face 26 by an amount of about twenty times the diameter of catheter 10. Therefore, to insure that the intensities of light in the fixed ratio of preselected light wavelengths remains constant, the tubing 40 should either extend distally a constant length beyond the face 26 (as in the embodiment of FIG. 4, to be described) or, if it is subject to variable extension or stick-out (as in the embodiment of FIGS. 1–3), it should extend at least that length beyond which the intensity of returned light is substantially constant (e.g. twenty times diameter of catheter tubing 12).

Figure 3:
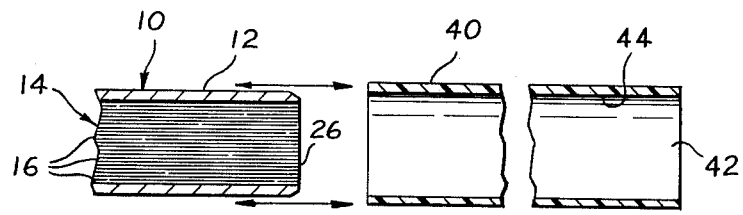
FIG. 3 is a view similar to that of FIG. 2 showing the calibration member removed from cooperative relationship with the catheter.

Referring to the embodiment illustrated in FIGS. 1 and 2 and assuming use for measuring oxygen saturation in blood, the catheter 10 and associated electro-optical equipment is initially calibrated using two samples of blood having respectively high and low known levels of oxygen saturation into which the distal end of the catheter is respectively immersed with the tube 40 removed (as shown in FIG. 3). The calibration standard value of a particular color of tube 40 is then determined by mounting the tube 40 on the distal end of catheter 10 as described and then measuring the fixed ratio of reflections (intensities) of the two light wavelength (805 mu./660 mu.) while the catheter and tube 40 are either in air or immersed in a clear liquid.

Subsequently, prior to use or reuse of catheter 10, it must in either case be sterilized e.g. by exposure to ethylene gas and then calibrated (or recalibrated) in conjunction with the associated electro-optical equipment. Inasmuch as a particular color of tubing 40 has previously been established as a calibration standard, that same piece of tubing or a similar piece of tubing of the same color is mounted on the distal end of catheter 10 and, with the catheter 10 and tubing 40 in air or immersed in a sterile clear liquid, the fixed ratio of the two light wavelengths previously established as being representative of a particular oxygen-in-blood concentration is used to calibrate the catheter and associated electro-optical equipment. When mounting the tube 40 on catheter 10 for the two aforementioned calibration operations, the tube should extend beyond face 26 a sufficient distance (e.g. 20 or more times the diameter of tubing 12) to insure constancy, as previously mentioned. Following such calibration, the tubing 40 is removed from the catheter 10 in a sterile manner and the distal end of the catheter is inserted into the cardiovascular system to perform the desired blood oxygen saturation measurements of the blood which flows past face 26 of the catheter.

Figure 4:
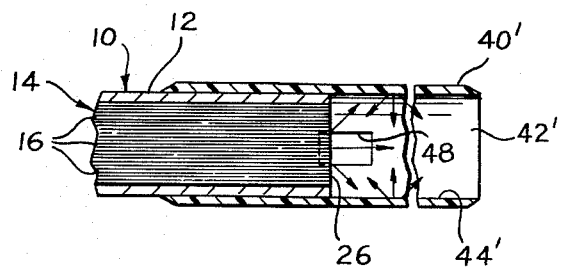
FIG. 4 is a view similar to that of FIG. 2 showing an alternate calibration member fixed on the catheter and having fluid flow porting therein.

FIG. 4 illustrates an alternate form of the invention in which a short length of tube or tubing 40' as for instance the vinyl tubing of the aforementioned embodiment, is permanently mounted on the distal end of catheter 10, as by bonding or the like, and remains affixed thereto during the calibration and the in-vivo introductions thereof into blood. Such an arrangement may be preferred where it is desired that a "support" structure be provided to prevent the vascular walls from occluding the catheter face 26, however tubing 40' is of sufficient flexibility to facilitate passage of it and the catheter 10 through the cardiovascular system. During actual measurements of blood oxygen concentration, blood is permitted to flow through tube 40' past face 26 of catheter 10 via passage 42' and one or more optional porting slots 48 through the walls of the tube 40'. Each porting slot 48 extends distally of face 26 from just rearwardly thereof to insure good blood flow past the face.

In the embodiment illustrated in FIG. 4, blood passing between catheter end face 26 and the inner surface 44' of tube 40' serves to reflect all or most of the light emitted from face 26. Because the inner surface 44' of tube 40' is constant as to length, position and color, its effect on the two wavelengths of light making up the ratio is constant and may be removed or cancelled from the sensed signals if it is found that the spacing between face 26 and inner surface 44' is so small as to permit some light to pass through the blood to the inner surface of the tube and back through the blood to face 26. Typically, the tube 40' extends only a short distance distally beyond the face 26 (e.g. one to five times the diameter of catheter tubing 12).

While alternate preferred embodiments of the invention have been shown and described, various modifications and substitutions may be made thereto without departing from the spirit and scope of the present invention. Accordingly, it is to be understood that the present invention has been described by way of illustration and not limitation.

What is claimed is:

1. In a fiber optic probe for use in measuring amounts of diffuse reflection of light from a target medium, said probe having light conducting fiber means and a housing tubing surrounding said light conducting fiber means, said light conducting fiber means extending between the proximal and distal ends of the housing tubing with the corresponding end faces thereof exposed at said proximal and said distal ends of the probe respectively, the improvement comprising:

reflecting means for establishing a calibration standard, said reflecting means having a generally tubular passage therein defining an interior surface, said tubular passage having a diameter at least as great as said light conducting fiber means, said reflecting means extending distally from the end face of said light conducting fiber means at the distal end of the housing tubing with said passage in registry with said light conducting fiber means, at least said interior surface of said reflecting means being a material which characteristically diffusely reflects and returns a fixed ratio of at least two preselected wavelengths of light directed thereupon from said exposed face of said light conducting fiber means at said distal end of said probe when said distal end exposed face of said fiber means and said reflecting means is disposed in air and clear fluids, said returned fixed ratio of light providing a calibration standard.

2. The fiber optic probe of claim 1 wherein said reflecting means extends distally from said end face at least a minimum length greater than which said fixed ratio of said at least two preselected wavelengths of returned light is substantially constant.

3. The fiber optic probe of claim 2 wherein said minimum extension length of said reflecting means is about at least twenty times the diameter of said housing tubing.

4. The fiber optic probe of claim 2 wherein said reflecting means removably embraces the housing of said optic probe.

5. The fiber optic probe of claim 4 wherein said probe is a catheter and said target medium is blood, said distal end of the catheter being disposed in said blood for said measurement of diffuse reflection of light therefrom and said reflecting means being removed from said catheter prior to said measurement in blood.

6. The fiber optic probe of claim 5 wherein said reflecting means and said interior surface thereof comprise a white pigmented plastic material.

7. The fiber optic probe of claim 5 wherein said tubular passage extends through said reflecting means.

8. The fiber optic probe of claim 1 wherein said probe is a catheter, said target medium is blood and said reflecting means is in fixed engagement with the housing of said probe.

9. The fiber optic probe of claim 8 wherein said reflecting means includes port means extending transversely therethrough adjacent the end face of said optical fiber means at the distal end of said probe for allowing blood to flow by said optical fiber means end face.

10. The fiber optic probe of claim 8 wherein said catheter is intended for use in measuring amounts of diffuse reflection of light from blood within the cardiovascular system of a living subject, said reflecting means being sufficiently rigid to prevent its collapse by contact with the cardiovascular walls to an extent which would occlude the end face of said light conducting fiber means at the distal end of said housing tubing and being sufficiently flexible to facilitate its passage within the cardiovascular system.

11. The fiber optic probe of claim 1 wherein said reflecting means and said interior surface thereof comprises a white pigmented plastic material.

12. The fiber optic probe of claim 1 wherein said light conducting fiber means comprises a multiplicity of light conducting fibers all being intimately juxtaposed adjacent said distal end of the probe, and the diameter of said passage and the positioning of said reflecting means place said passage in registry with said multiplicity of light conducting fibers.

13. The fiber optic probe of claim 1 wherein the diameter of said passage in said reflecting means is at least as great as the exterior diameter of said probe housing tubing and said reflecting means additionally extends rearwardly of said distal end of the probe in encircling relationship therewith.

14. In a fiber optic catheter for use in measuring amounts of diffuse reflection of light in blood, said catheter having light-conducting fiber means and a catheter tubing surrounding said fiber means, said fiber means extending between the proximal and distal ends of the catheter tubing with corresponding end faces thereof exposed at said proximal and distal ends of the catheter respectively, a reflecting member cooperatively associated with said catheter adjacent the distal end thereof serving to characteristically diffusely reflect and return a fixed ratio of at least two preselected wavelengths of light directed thereupon from said exposed face of said light-conducting fiber means at said distal end of said catheter when said distal end exposed face of said fiber means and said reflecting member are disposed in air and clear fluids for establishing a calibration standard, the improvement wherein said reflecting member comprises a tube of white pigmented plastic material, said tube having a proximal portion in concentric removable embracing relationship with said distal end of said catheter tubing and a distal portion extending distally beyond said distal end of said catheter, said tube distal portion having an interior surface of said white plastic material for said diffuse reflection of said two preselected wavelengths of light.

15. The method of calibrating and using a fiber optic probe to measure amounts of diffuse reflection of light from blood, said probe having light conducting fiber means in a housing tubing surrounding said light conducting fiber means, said light conducting fiber means extending between the proximal and distal ends of the housing tubing with the corresponding end faces thereof exposed at said proximal and said distal ends of the probe respectively, comprising the steps of:

positioning a reflecting means having a generally tubular passage therein adjacent to said light conducting fiber means at the distal end of said housing tubing, said tubular passage having a diameter at least as great as said light conducting fiber means and being in optical registry therewith, said tubular passage defining an interior surface in said reflecting means, said interior surface being of a material which characteristically diffusely reflects and returns a fixed ratio of at least two preselected wavelengths of light directed thereupon from said exposed face of said light conducting fiber means at said distal end of said probe when said distal end exposed face of said fiber means and said reflecting means is disposed in air and clear fluids, said returned fixed ratio of light providing a calibration standard;

disposing said distal end exposed face of said fiber means and said reflecting means adjacent thereto in air or a clear fluid to establish said calibration standard; and subsequently disposing at least said exposed face of said light conducting fibers in blood for measuring the diffuse reflection of light from the blood.

16. The method of claim 15 further including the step of removing said reflecting means from said position adjacent said distal end exposed face of said fiber means following said disposing in air or clear fluid to establish said calibration standard and prior to said disposing in blood for measuring said amounts of diffuse reflection of light from the blood.

17. The method of claim 15 wherein said reflecting means comprises flexible tubing which remains affixed to said housing tubing during said disposing in blood for measuring said amounts of diffuse reflection of light from the blood.

* * * * *